United States Patent [19]

Dhabhar

[11] Patent Number: 4,569,955

[45] Date of Patent: Feb. 11, 1986

[54] DENTURE ADHESIVE

[75] Inventor: Dadi J. Dhabhar, Norwalk, Conn.

[73] Assignee: Richardson-Vicks Inc., Wilton, Conn.

[21] Appl. No.: 715,255

[22] Filed: Mar. 25, 1985

Related U.S. Application Data

[63] Continuation of Ser. No. 476,319, Mar. 17, 1983, abandoned.

[51] Int. Cl.$^4$ .............................................. A61K 5/06
[52] U.S. Cl. ...................................... 523/120; 106/35; 260/998.11; 433/168.1; 433/180; 524/45
[58] Field of Search ................ 523/120; 433/168, 180; 106/35; 260/998.11; 524/45

[56] References Cited

U.S. PATENT DOCUMENTS

| | | | |
|---|---|---|---|
| 3,003,988 | 10/1961 | Germann et al. | 260/33.6 |
| 3,215,599 | 11/1965 | Westfield et al. | 167/63 |
| 3,736,274 | 5/1973 | Schoenholz et al. | 523/120 |
| 4,280,936 | 7/1981 | Dhabhar et al. | 523/120 |
| 4,373,036 | 2/1983 | Chang et al. | 523/120 |

Primary Examiner—Lorenzo B. Hayes
Attorney, Agent, or Firm—Salvatore R. Conte

[57] ABSTRACT

An improved denture adhesive containing an adhesive polymeric fraction comprising an admixture of mixed, partial salts of lower alkyl vinyl ether-maleic anhydride-type copolymers with sodium carboxymethylcellulose in a vehicle comprising mineral oil thickened with polyethylene having a molecular weight of from about 1000 to 21,000.

20 Claims, No Drawings

DENTURE ADHESIVE

This a continuation of application Ser. No. 476,319 filed Mar. 17, 1983, now abandoned.

FIELD OF THE INVENTION

This invention relates to an improved denture adhesive formulation that possesses improved thermal and viscosity stability over the temperature range of 10° to 48° C. and is unexpectedly less thixotropic at both 25° and 37° C. exhibiting greatly reduced shear sensitivity at the mouth temperature of 37° C. thereby providing a denture adhesive product that oozes either not at all or only minimally during use.

BACKGROUND OF THE INVENTION

Denture adhesive cream formulations have heretofore been comprised mainly of natural or synthetic polymer materials suspended in an anhydrous oleagenous vehicle system comprising mineral oil and petrolatum. The petrolatum is added to thicken the formulation consistency to that of a cream which is extrudable from tubes. These formulations necessarily must be thick to prevent syneresis or phase separation because the solid adhesive particles are merely suspended in the oily vehicle. This thickness of the formulations makes them somewhat difficult to squeeze out from the tube.

Additionally, although these formulations are fairly thick in consistency at ambient room temperature of about 25° C., they are not thermally very stable and hence tend to thin out even at slightly elevated temperatures. For example, at the body/mouth temperature of 37° C. at which these formulations are used, they tend to thin out and become runny and therefore ooze out from under the denture during use. The phenonenon is naturally further aggravated when hot liquids and foods are consumed by denture wearers who use such denture adhesive products. This problem with oozing of denture adhesive from under the dentures into the mouth is considered to be one of the major drawbacks to the consumer due to the unpleasant taste and mouth feel. Additionally, the holding property of the formulation is reduced due to the oozing or loss of product from under the denture.

Oil separation is an additional drawback to such denture creams in addition to the substantial change in viscosity of such products over the temperature range of 10° to 48° C.

It is therefore highly desirable that improved denture adhesives be made available which avoid or substantially reduce these drawbacks of prior art denture adhesives.

SUMMARY OF THE INVENTION

It has now been surprisingly discovered that denture adhesives which eliminate or substantially avoid the hereinbefore mentioned drawbacks are provided by denture adhesives containing an adhesive polymeric fraction comprising an admixture of mixed, partial salts of lower alkyl vinyl ether-maleic anhydride-type copolymers with sodium carboxymethylcellulose in a vehicle comprising mineral oil thickened with polyethylene having a molecular weight in the range of from about 1,000 to about 21,000.

DETAILED DESCRIPTION OF THE INVENTION

This invention relates to a denture adhesive composition which, when in contact with saliva, hydrates within the oral cavity to provide superior adherent properties. The composition comprises two essential components. The first is an adhesive fraction comprising an admixture of a mixed, partial salt of lower alkyl vinyl ether-maleic anhydride-type copolymer with sodium carboxymethylcellulose. The second is a vehicle comprising mineral oil and a low molecular weight polyethylene having a molecular weight in the range of from about 1,000 to about 21,000.

With regard to the adhesive component, the mixed, partial salts of lower alkyl vinyl ether-maleic anhydride-type copolymers and the sodium carboxymethylcellulose constituents are well known and have been used heretofore to stabilize and secure dentures.

In U.S. Pat. No. 3,003,988, issued Oct. 10, 1961 to D. P. Germann et al. and entitled "Stabilizer for Dentures", there are described certain water-sensitized, but water-insoluble, materials for stabilizing dentures which are synthetic, hydrophilic, colloidal materials comprising mixed, partial salts of lower alkyl vinyl ether-maleic anhydride-type copolymers. It is these very same mixed, partial salts that are utilized as part of the adhesive component of this invention and, accordingly, the written description of said mixed, partial salts and the method and examples of preparing same which is set forth in said U.S. Pat. No. 3,003,988 is incorporated herein and made a part of this specification by reference thereto.

Said mixed, partial salts are particularly defined in the claimed composition of claim 1 of said U.S. Pat. No. 3,003,988 as follows:

" . . . a water-insoluble water-sensitized polymeric material; said material characterized by a particle size of minus 150-mesh U.S.B.S. sieve, by an apparent bulk density greater than 0.5 gram per cubic centimeter, and by a pH between 5 and 8.5, the pH being determined on a one percent by weight aqueous dispersion of said material in water; said material consisting essentially of a partial mixed salt of a copolymer selected from the group consisting of copolymers and partial lower alkyl esters of these copolymers, said copolymers consisting essentially of the repeated structural unit,

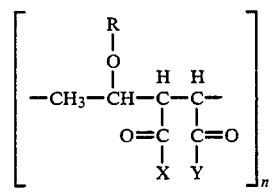

wherein X and Y separately each represent a hydroxyl radical and X and Y together represent a bivalent oxygen atom, R represents an alkyl radical of less than 5 carbon atoms, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial lower alkyl esters of said copolymers having less than one-third of the total initial carboxyl groups esterified, said partial mixed salts containing calcium cations and alkali cations, in a mole ratio between 1:1 and 5:1, the alkali cations selected from the group consisting of sodium, potassium, and quaternary ammonium cations, with not more than one third of the total initial carboxyl groups unreacted."

For purposes of convenience, the aforementioned mixed, partial salts will be generically referred to in this specification and claims hereinafter as mixed, partial salts of lower alkyl vinyl ether-maleic anhydride-type copolymer and also denoted by the abbreviated term, "mixed, partial salts of AVE/MA copolymer". The preferred mixed, partial salts of AVE/MA copolymer for purposes of this invention are those indicated as preferred or with the preferred specifications denoted in said U.S. Pat. No. 3,003,988.

The most preferred mixed, partial salts of AVE/MA copolymer for use in the adhesive compositions of this invention are the calcium-sodium partial salts of a methyl vinyl ether-maleic anhydride (MVE/MA) copolymer with about 20–36 percent of the total initial carboxyl groups of the copolymer unreacted, a calcium-to-sodium mole ratio of from about 2.5:1 to about 4:1 per initial carboxyl group, an apparent bulk density of about 0.5 gram per cubic centimeter as a minimum and substantially from about 0.7 to about 0.9 gram per cubic centimeter, and a pH of about 6–7.5 for the powder at a concentration of 1 percent by weight in water. For purposes of convenience, these most preferred mixed, partial salts will be referred to hereinafter by the abbreviated term, "Ca/Na partial salts of MVE/MA copolymer".

In Example VI of the aforementioned Germann et al. U.S. Pat. No. 3,003,988, a calcium-sodium partial salt of mixed vinyl ether-maleic anhydride (MVE/MA) copolymer is described with about 30 percent of the total initial groups of the copolymer unreacted, a calcium-to-sodium equivalent ratio of 0.51:0.19 (i.e., about 2.6:1) per initial carboxyl group, an apparent bulk density of 0.88 gram per cubic centimeter, and a pH of 7.5 for the powder at a concentration of 1 percent by weight in water. This particular 2.6:1 Ca:Na partial salt, which is among the preferred, mixed partial salts utilized in this invention, is prepared by reacting aqueous solutions of calcium acetate and sodium hydroxide with the MVE/MA copolymer (Note: in U.S. Pat. No. 3,003,988, said MVE/MA copolymer is denoted as PVM/MA copolymer).

The preparation of another preferred Ca/Na partial salt is shown in Example VII of the '988 patent, wherein the calcium-to-sodium equivalent ratio is 0.5:0.134 (i.e., about 3.75:1), with about 35 percent of the total initial groups of the copolymer unreacted, an apparent bulk density of 0.92 gram per cubic centimeter, and a pH of 6.2 for the powder at a concentration of 1 percent by weight in water. This particular 3.75:1 Ca:Na partial salt is prepared by reacting aqueous solutions of calcium acetate and sodium acetate with the MVE/MA copolymer.

Among the most preferred Ca/Na partial salts of MVE/MA copolymer is the calcium-sodium partial salt with about 20 percent of the total initial carboxyl groups of the copolymer unreacted, a calcium-to-sodium mole ratio of about 3.5:1 per initial carboxyl group, an apparent bulk density of about 0.8–0.95 gram per cubic centimeter, and a pH of about 6.3–7.4 for the powder at a concentration of 1 percent by weight in water. For purposes of convenience, this particular most preferred Ca/Na partial salt will be referred to hereinafter by the abbreviated term, "3.5:1 Ca:Na partial salt of MVE/MA copolymer".

This most preferred Ca/Na partial salt may be obtained by following the procedures of the aforementioned Examples VI and VII of the '988 patent by, for example, utilizing aqueous solutions of sufficient calcium acetate and sodium hydroxide (via Example VI) or calcium acetate and sodium acetate (via Example VII) to yield the desired Ca:Na ratio upon reaction with the appropriate MVE/MA copolymer.

Sodium carboxymethylcellulose is a powder which, when moistened, becomes hydrated and tacky or gummy in consistency with adhesive characteristics. The sodium carboxymethylcellulose "gums" employed in this invention are water soluble, anionic, long chain polymers, derived from cellulose. Properties vary with the average number of carboxy methyl groups that are substituted per anhydroglucose unit in each cellulose molecule. This property is generally referred to as "the degree of substitution", with the maximum substitution possible designated as "3.0" since there are just three hydroxy groups capable of reaction in each anhydroglucose unit. For the practice of this invention, it has been found that one or more such cellulose gums having a degree of substitution of from about 0.4 to about 1.2 is suitable. The viscosity of a 1 percent solution of the gum, measured at 25° C., should be in the range of from about 400 to 4,500, preferably 1,500 to 2,500 centipoises.

Sodium carboxymethylcellulose gums of this type are more fully described in "Chemical and Physical Properties: Cellulose Gum," 1978, published by Hercules, Incorporated, Coatings and Specialty Products Department, 910 Market Street, Wilmington, Del. 19899.

As examples of commercially available sodium carboxymethylcellulose gums suitable for use in this invention there may be mentioned those sold by Hercules, Incorporated, Wilmington, Del., as types 4H1, 7H, 9H4, 7H3S, 7HOF and 7H4. Type 7H3S is preferred for use in this invention.

The adhesive polymeric fraction of the denture adhesives of this invention comprise from about 50 to about 95 weight percent of the mixed, partial salts of lower alkyl vinyl ether-maleic anhydride-type copolymers and from about 5 to about 50 weight percent sodium carboxymethylcellulose, preferably from about 85 to about 95 percent of the copolymer and from about 5 to about 15 percent sodium carboxymethylcellulose, and most preferably about 90 percent copolymer and 10 percent sodium carboxymethylcellulose.

The adhesive portion of the total denture adhesive formulation comprises an effective adhesive amount of the admixture of the mixed partial salts of lower alkyl vinyl ether-maleic anhydride-type copolymer with sodium carboxymethylcellulose. Most generally the admixture will comprise from about 25 to about 60 weight percent of the total denture adhesive formulation and the vehicle component along with other miscellaneous minor additives will comprise from about 40 to about 75 weight percent. Preferably the admixture will comprise from about 45 to about 55 percent and even more preferably from about 50 to 53 weight percent and most preferably about 52.5 weight percent. Similarly the vehicle and other additives will preferably then comprise from about 45 to about 55 percent, even more preferably from about 47 to 50 percent and most preferably about 47.5 percent.

The vehicle component of the denture adhesive formulations of this invention comprises a blend of mineral oil and low molecular weight polyethylene. A mineral oil of any suitable viscosity may be used in the practice of this invention. Preferably a highly refined white oil having a viscosity of about 50–350 seconds at 38° C. and meeting United States Pharmacopeia specifications as to taste, odor and acid tests is preferred.

The low molecular weight polyethylene polymers suitable for use in the practice of this invention have an average molecular weight ranging from about 1,000 to about 21,000, preferably from about 2,000 to about 5,000. Powdered polyethylene polymers having an average molecular weight of about 2,000 are especially preferred.

As examples of commercially available powdered polyethylene products suitable for use in this invention, there may be mentioned those sold by Allied Chemical Company, Morristown, N.J., under the name A-C Polyethylene 6A, A-C Polyethylene 8A, A-C Polyethylene 9A, A-C Polyethylene 6AF, A-C Polyethylene 8AF and A-C Polyethylene 9AF. Similarly, powdered polyethylene products sold by United States Industries, Park Avenue, New York 10017, as their Microthene series are also suitable. Preferred for use in this invention is A-C Polyethylene 6-A.

In the vehicle components of the denture adhesive formulations of the invention, the mineral oil and polyethylene are used in amounts of from about 3 to about 20 percent, preferably about 5 to about 15 percent, and most preferably about 11 percent polyethylene and from about 80 to 97 weight percent, preferably about 85 to about 95 percent and most preferably about 89 percent of mineral oil, based on the total weight of the vehicle components. In terms of the total weight of the entire denture adhesive formulation, the polyethylene is generally employed in an amount of from about 1.2 to about 15 weight percnt, preferably from about 2.0 to about 11.25 percent and most preferably about 5 percent and the mineral oil is generally employed in an amount of from about 32 to about 72.75 weight percent, preferably from about 34 to about 72.25 percent and most preferably about 42.4 percent.

Any suitable flavoring agent, thickener such as silica, colorants or other optional ingredients generally employed in denture adhesives may be added, if desired, so long as their addition is not detrimental to the overall adhesive ability of the denture adhesive composition.

A particularly preferred vehicle for use in the denture adhesives of this invention is the blend of polyethylene and mineral oil described in U.S. Pat. No. 3,215,599, issued Nov. 2, 1965 to P. Than et al. and assigned to Warner-Lambert Pharmaceutical Company, the disclosure of which is incorporated herein by reference thereto. The vehicle mixture of polyethylene and mineral oil is preferably prepared by adding the polyethylene to the mineral oil by melting it in the mineral oil at about 90° C. with stirring and then allowing this mixture to either cool gradually or with rapid shock cooling while stirring vigorously.

At a temperature of 50° C. or below, the adhesive components are added to the vehicle and mixed in. Additives such as flavoring agents, thickeners such as silica, flavorants and the like may also be incorporated in the polyethylene-mineral oil vehicle.

By employing the polyethylene-mineral oil vehicle with the specific adhesive component admixture in accordance with this invention, an improved denture adhesive is obtained which is easy to squeeze from a tube, does not thin out excessively at the mouth temperature of 37° C., has substantially less oil separation, and greatly improved viscosity and thermal stability over the range of from about 10° to about 48° C. and additionally, unexpectedly much less thixotropic with greatly reduced shear sensitivity at 25° and 37° C. despite the known propensity for low density polyethylenes of the type used in this invention to produce gels of a thixotropic nature. The greatly reduced shear sensitivity of the adhesive formulations of this invention is a beneficial effect for denture adhesive cream products. The products during use under the denture is constantly subjected to shear of biting forces and since the adhesive products of this invention are more shear stable at the 37° C. mouth temperature, the product will not ooze or only ooze minimally compared to a similar product but employing the prior art mineral oil-petrolatum vehicle.

The following example is illustrative but not limiting of the improved dentifrice adhesive compositions of this invention.

EXAMPLE

| Component | % w/w Based on Total Formulation |
|---|---|
| Ca/Na Salt[1] | 47.25 |
| Na—CMC[2] | 5.25 |
| Mineral Oil heavy | 41.36 |
| Polyethylene[3] | 5.00 |
| Thickener[4] | 1.10 |
| Colorant[5] | 0.04 |

[1]3.5:1 Ca:Na partial salt of MVE/MA copolymer
[2]Sodium carboxymethylcellulose - type 7H3S
[3]Polyethylene - AC-6A
[4]Silica - Cab-O-Sil M5
[5]Opatint - X-01854

The denture adhesive cream of this example was prepared in the following manner. The mineral oil colorant and polyethylene were placed in a metal container and heated to about 90° C. while mixing and stirring. The solution was placed in a water bath of 50° C. water to cool the solution to about 60° C. after which it is removed from the water bath and slow cooled to a temperature of about 50° C. with stirring and scraping of the bottom and sides of the container as the solution thickens to a gel consistency. The copolymer, sodium carboxymethylcellulose and silica are mixed together and added to the gel solution while mixing on speed #1 on a HOBART K.A. mixer for about one hour until a smooth product is obtained.

A comparative product employing the prior art mineral oil-petrolatum vehicle of the prior art was prepared in a similar manner. The comparative product was formulated with an amount of mineral oil-petrolatum to provide a product of the same viscosity at 25° C. as the viscosity of the product of the Example so as to allow a proper comparison. The composition of the comparative product was as follows:

| Component | % w/w Based On Total Formulation |
|---|---|
| Ca/Na salt[1] | 47.25 |
| Na—CMC[2] | 5.25 |

-continued

| Component | % w/w Based On Total Formulation |
|---|---|
| Mineral oil, heavy | 26.25 |
| Petrolatum | 20.11 |
| Thickener[3] | 1.10 |
| Colorant[4] | 0.04 |

[1]3.5:1 Ca:Na partial salt of MVE/MA copolymer
[2]Sodium carboxymethylcellulose - type 7H3S
[3]Silica - Cab-O-Sil M5
[4]Opatint - X-01854

The levels of petrolatum-mineral oil used was such that the viscosities of the two products were the same at 25° C. The viscosities of the product of this invention and the comparative product was then measured at other temperatures both above and below 25° C., from a low of 10° C. to a high of 48° C. The viscosity data for these two products is shown in the following Table I.

TABLE I

| | Brookfield Viscosity - cps | |
|---|---|---|
| Temperature °C. | Example Product | Comparative Product |
| 10 | 545,833 | 1,000,000+ |
| 17 | 482,500 | 662,500 |
| 25 | 442,500 | 442,500 |
| 37 | 239,167 | 90,833 |
| 42 | 155,833 | 29,667 |
| 48 | 125,000 | 18,500 |

At elevated temperature, the comparative product showed a dramatic loss in viscosity wherein the Example of this invention showed only a modest drop in viscosity. Conversely, at lower temperatures, the comparative product showed a dramatic gain in viscosity whereas the composition of the Example showed only a very slight gain in viscosity. The product of this invention is much more stable over a fairly wide range of temperatures and thus would ooze out from under the dentures much less than the comparative product. Moreover, the product of this invention is much more easily squeezed out of a tube at lower temperatures than is the comparative product due to its much lower viscosity at 17° and 10° C.

Additionally, the thixotropy of these two products was measured at 25° C. and 37° C. using a Ferrante-Shirley viscometer using a medium cone by obtaining hysteresis loops and measuring the area under the hysteresis loop to determine the measure of thioxotropic behavior of the products as per J. Freling, Monitor Bath Qaulity with Rheograms, Instrumentation Technology, pp. 41–45, June 1982. The measurement of thixotropy for these two products is set forth in the following Table II.

TABLE II

| | Area of Hysteresis (sq. mm.) | |
|---|---|---|
| Temperature °C. | Example Product | Comparative Product |
| 25 | 3249 | 7005 |
| 37 | 3864 | 6190 |

The data indicates that at both 25° and 37° C. the product of this invention is less thixotropic than the comparative product; a finding which is unexpected because the use of polyethylene in mineral oil is recommended for obtaining thixotropic gels. The greatly reduced thixotropy or shear sensitivity of the product of this invention, especially at 37° C., is a highly beneficial effect for denture adhesive cream products. Since the product, during use under the denture is constantly subjected to shear from biting forces and since the product is more shear stable at the mouth temperature of 37° C., it would not ooze or only ooze minimally during use.

I claim:

1. A denture adhesive composition consisting essentially of a mixture of:
   (a) an effective adhesive amount of an adhesive polymeric fraction consisting essentially of a mixed, partial salt of a lower alkyl vinyl ether-maleic anhydride copolymer and sodium carboxymethylcellulose in
   (b) a vehicle consisting essentially of mineral oil thickened with polyethylene having an average molecular weight of from about 1000 to about 21,000.

2. The composition of claim 1 consisting essentially of a mixture of from about 25 to about 60 percent w/w of the adhesive polymeric fraction of a mixed, partial salt of AVE/MA copolymer and sodium carboxymethylcellulose and from about 40 to about 75 percent w/w of the vehicle of mineral oil thickened with polyethylene.

3. The composition of claim 2 wherein the adhesive polymeric fraction consists essentially of from about 45 to 55 percent w/w and the vehicle comprises from about 45 to 55 percent w/w.

4. The composition of claim 3 wherein the adhesive polymeric fraction comprises from about 50 to 53 percent w/w and the vehicle comprises from about 47 to about 50 percent w/w.

5. The composition of claim 4 wherein the adhesive polymeric fraction consists essentially of about 52.5 percent w/w and the vehicle comprises about 47.5 percent w/w.

6. The composition of claim 1 wherein the amount of polyethylene is from about 1.2 to about 15 percent w/w and the mineral oil from about 32 to about 72.75 percent w/w.

7. The composition of claim 6 wherein the amount of polyethylene is from about 2.0 to about 11.25 percent w/w and the mineral oil from about 34 to 71.25 percent w/w.

8. The composition of claim 7 wherein the amount of polyethylene is about 5 percent w/w and the mineral oil about 41.4 percent w/w.

9. The composition of claim 4 wherein the amount of polyethylene is from about 1.2 to about 15 percent w/w and the mineral oil from about 32 to about 72.75 percent w/w.

10. The composition of claim 9 wherein the amount of polyethylene is from about 2.0 to about 11.25 percent w/w and the mineral oil from about 34 to 71.25 percent w/w.

11. The composition of claim 10 wherein the amount of polyethylene is about 5 percent w/w and the mineral oil about 41.4 percent w/w.

12. The composition of claim 1 wherein said mixed, partial salt is a Ca/Na partial salt of methyl vinyl ether-maleic anhydride copolymer.

13. The composition of claim 1 wherein said mixed, partial salt is a 3.5:1 Ca:Na partial salt of methyl vinyl ether-maleic anhydride copolymer.

14. The composition of claim 4 wherein said mixed, partial salt is a Ca/Na partial salt of methyl vinyl ether-maleic anhydride copolymer.

15. The composition of claim 4 wherein said mixed, partial salt is a 3.5:1 Ca:Na partial salt of methyl vinyl ether-maleic anhydride copolymer.

16. The composition of claim 7 wherein said mixed, partial salt is a Ca/Na partial salt of methyl vinyl ether-maleic anhydride copolymer.

17. The composition of claim 7 wherein said mixed, partial salt is a 3.5:1 Ca:Na partial salt of methyl vinyl ether-maleic anhydride copolymer.

18. The composition of claim 9 wherein said mixed, partial salt is a Ca/Na partial salt of methyl vinyl ether-maleic anhydride copolymer.

19. The composition of claim 9 wherein said mixed, partial salt is a 3.5:1 Ca:Na partial salt of methyl vinyl ether-maleic anhydride copolymer.

20. The composition of claim 8 wherein said mixed, partial salt is a 3.5:1 Ca:Na partial salt of methyl vinyl ether-maleic anhydride copolymer.

* * * * *